United States Patent [19]
Fleck

[11] 3,956,283
[45] May 11, 1976

[54] BIS-(TRIAZINYLAMINO)-STILLENE DERIVATIVES

[75] Inventor: Fritz Fleck, Bottmingen, Switzerland

[73] Assignee: Sandoz Ltd., Basel, Switzerland

[22] Filed: May 16, 1974

[21] Appl. No.: 470,523

[52] U.S. Cl. .............................. 260/240 B; 8/1 W; 162/162; 252/301.23; 427/158
[51] Int. Cl.² .............................. C07D 403/10
[58] Field of Search .............................. 260/240 B

[56] References Cited

UNITED STATES PATENTS

| | | | |
|---|---|---|---|
| 3,018,287 | 1/1962 | Fleck | 260/240 B |
| 3,464,886 | 9/1969 | Paul | 260/240 B |
| 3,479,349 | 11/1969 | Allison et al. | 260/240 B |
| 3,600,385 | 8/1971 | Loffelman et al. | 260/240 B |
| 3,757,010 | 9/1973 | Balzer et al. | 260/240 B |

FOREIGN PATENTS OR APPLICATIONS

| | | |
|---|---|---|
| 1,051,986 | 12/1966 | United Kingdom |
| 1,313,469 | 4/1973 | United Kingdom |
| 1,243,276 | 8/1971 | United Kingdom |

*Primary Examiner*—Arthur P. Demers
*Attorney, Agent, or Firm*—Gerald D. Sharkin; Richard E. Vila; Joseph J. Borovian

[57] ABSTRACT

Disclosed are compounds of formula I,

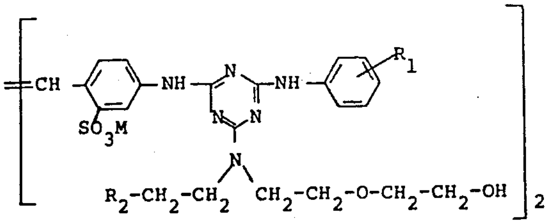

I in which $R_1$ signifies hydrogen, fluorine, bromine, chlorine, $C_{1-6}$alkyl, $C_{1-6}$alkoxy or $—SO_3M$,
$R_2$ signifies cyano or $—CONR_3R_4$,
in which either $R_3$ and $R_4$, independently, each signify hydrogen, $C_{1-6}$ alkyl or $C_{2-6}$ hydroxyalkyl,
or $R_3$ and $R_4$, together with the nitrogen atom to which they are attached, signify a pyrrolidino, piperidino or morpholino ring, and
M signifies hydrogen or a non-chromophoric cation, their production and use as optical brightening agents, particularly for cellulosic substrates such as paper and cotton.

39 Claims, No Drawings

BIS-(TRIAZINYLAMINO)-STILLENE DERIVATIVES

IMPROVEMENTS IN OR RELATING TO ORGANIC COMPOUNDS

The invention relates to stilbene compounds.

The invention provides compounds of formula I,

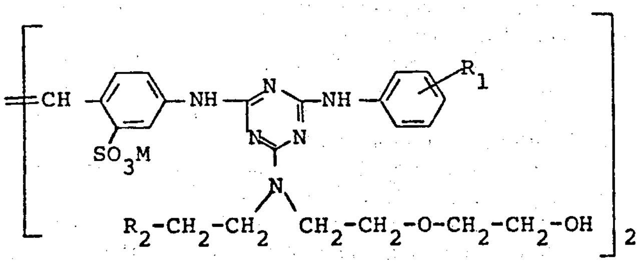

I in which $R_1$ signifies hydrogen, fluorine, bromine, chlorine, $C_{1-6}$ alkyl, $C_{1-6}$ alkoxy or $-SO_3M$, $R_2$ signifies cyano or $-CONR_3R_4$, in which either $R_3$ and $R_4$, independently, each signify hydrogen, $C_{1-6}$ alkyl or $C_{2-6}$ hydroxyalkyl, or $R_3$ and $R_4$, together with the nitrogen atom to which they are attached, signify a pyrrolidino, piperidino or morpholino ring, and M signifies hydrogen or a non-chromophoric cation.

Any halogen as $R_1$ is preferably chlorine. Any alkyl or alkoxy radical as $R_1$ is preferably of 1 to 4 carbon atoms, examples of such alkyl radicals and alkyl moieties in alkoxy radicals being methyl, ethyl, n-propyl, isopropyl, n-butyl, isobutyl, sec.butyl, and tert.butyl, the most preferred alkyl and alkoxy radicals being the methyl and methoxy radicals, respectively. $R_1$ preferably signifies chlorine, $C_{1-4}$alkoxy, $C_{1-4}$alkyl or hydrogen, more preferably $C_{1-4}$alkyl or hydrogen.

As examples of amines $NHR_3R_4$, from which corresponding amides as $R_2$ may be derived, include methylamine, ethylamine, ethanolamine, isopropanolamine, butylamine, dimethylamine, diethylamine, diethanolamine as well as pyrrolidine, piperidine and morpholine. However, $R_3$ and $R_4$ preferably signify hydrogen.

Where M signifies a cation, the exact nature thereof is not critical provided such cation is nonchromophoric. Cations conventional in the optical brightener art are preferred. As examples of suitable cations may be given those of the alkali metals, e.g., lithium, potassium and sodium, those of the alkaline earth metals, e.g., magnesium, calcium, strontium and barium, and those of ammonia and substituted or unsubstituted alkyl amines, such as of formula $R_5R_6R_7N^+H$ where $R_5$, $R_6$ and $R_7$, independently, signify hydrogen or $C_{1-4}$alkyl, unsubstituted or substituted by up to two, preferably one, hydroxy group, e.g., mono-, di- and triethanolammonium and mono-, di- and tri-isopropanolammonium cations. The most preferred cation is sodium. For the sake of simplicity, M has been shown in the formulae herein as monovalent. It may, of course, be polyvalent, e.g., divalent when signifying an alkaline-earth metal cation.

As a preferred group of compounds of formula I may be given those in which $R_1$ signifies hydrogen, chlorine, $C_{1-4}$ alkyl or $C_{1-4}$ alkoxy, and $R_2$ signifies $-CN$ or $-CONH_2$, M being as defined in formula I.

As a further preferred group of compounds of formula I may be given those in which $R_1$ signifies hydrogen or $C_{1-4}$alkyl, particularly hydrogen or methyl, and $R_2$ signifies $-CN$ or $-CONH_2$, M being as defined in formula I.

The invention also provides a process for the production of compounds of formula I, comprising reacting, in any desired order, a cyanuro halide with a compound of formula II,

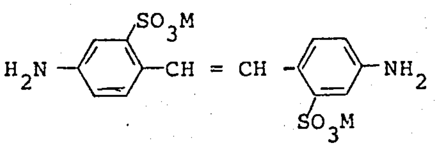

II in which M is as defined above, an amine of formula III,

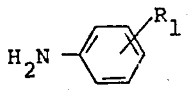

III

, in which $R_1$ is as defined above, and an amine of formula IV, $$R_2-CH_2-CH_2-NH-CH_2-CH_2-O-CH_2-CH_2-OH \qquad IV$$

in which $R_2$ is as defined above, in free base or acid addition salt form.

The process may be carried out in conventional manner.

As will be appreciated the mol ratio of cyanuro halide: compound of formula II: amine of formula III: amine of formula IV is preferably 2:1:2:2.

The process is conveniently carried out in an aqueous medium or in an aqueous-organic medium, e.g., by dissolving the cyanuro halide in an organic solvent, such as acetone, benzene, toluene and chlorobenzene, and adding thereto dropwise the amine compound in aqueous medium. It is preferred to use a dispersing agent for more rapid reaction and purer products.

For the first reaction with the cyanuro halide, i.e., substitution of the first halogen atom thereof, a temperature of from 0° to 15°C is preferably employed. The preferred pH range for such reaction is from 1 to 7. For the second reaction with the cyanuro halide, i.e., substitution of the second halogen atom thereof, the preferred reaction temperature is from 20° to 60°C. The preferred pH range for such reaction is from 4 to 8. For the third reaction with the cyanuro halide, i.e., substitution of the third halogen atom thereof, a preferred reaction temperature is from 60° to 100°C. The preferred pH range is from 4 to 10.

The hydrochloric acid freed during each step of the reaction is conveniently neutralised by addition of alkalis, e.g., alkali-metal hydroxides, bicarbonates or carbonates or tertiary amines such as tris-[2-hydroxyethyl]-amine.

As an example of the order of reaction may be given firstly reacting the cyanuro halide with the amine of formula III, secondly reacting the product thereby formed with the diamine of formula II and, thirdly, reacting the product so formed with the amine of formula IV. The preferred order of reaction, however, is firstly reaction of the cyanuro halide with the diamine of formula II, secondly, reaction of the product formed thereby with the amine of formula III and, thirdly, reaction of the product so formed with the amine of formula IV.

Thus, the preferred last step of the process and which forms an aspect of the present invention, is the reaction of a compound of formula V,

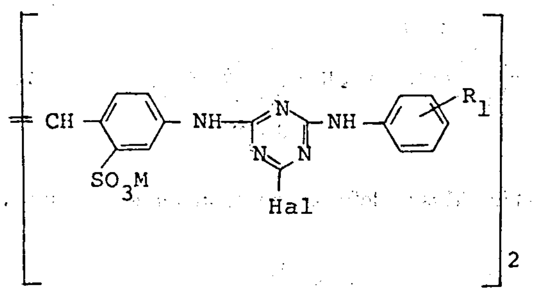

V in which M and $R_1$ are as defined above, and Hal signifies a halogen atom, with an amine of formula IV, above, which is in free base or acid addition salt form.

The preferred cyanuro halides are cyanuro chloride and bromide, the former being particularly preferred.

The compounds of formula I may be isolated and purified in conventional manner, e.g., by salting out, acidification or evaporation techniques. Liquid preparations of the compounds of formula I in salt form may be obtained by addition of solvent aids, such as glycol, glycolic ether, formamide acetamide, urea and mono-, bit- or tris-(2-hydroxyethyl)- or -(2-hydroxypropyl)-amine.

The compounds of formula II, III and IV are known or may be obtained in conventional manner from available startig materials.

As examples of compounds of formula III may be given o-, m- and p-toluidines, 1-amino-4-ethylbenzene, 1-amino-2-ethylbenzene, 1-amino-3-ethylbenzene, 1-amino-4-methoxybenzene, 1-amino-3-methoxybenzene, 1-amino-2-methoxybenzene, o-, m- and p-fluoroaniline, o-, m- and p-chloroaniline and aniline.

The compounds of formula IV may, for example be obtained by reacting an amine of formula VI, $$NH_2—CH_2—CH_2—O—CH_2—CH_2—OH \qquad VI$$

in free base or acid addition salt form, e.g., chlorohydrate salt form, with compounds of formula VII $$R_2—CH=CH_2 \qquad VII$$

in which $R_2$ is as defined above,

The compounds of formula I are useful as optical brightening agents, particularly for optically brightening cellulosic substrates.

The substrate to be brightened may be in any desired form, e.g., loose fibre, thread, yarn, woven, non-woven, paper, felt, velvet or carpet form and may comprise blends of cellulosics with non-cellulosics. The substrate may also be brightened in the mass, e.g., where produced from viscose.

Particular applications of the compounds of formula I are as follows:

a. the brightening of cellulosic textiles, particularly cotton, from a long bath,
b. the brightening of cellulosic textiles, particularly cotton, from the washing liquor,
c. the brightening of viscose-artificial silk by application of the compounds of formula I in the spinning mass during the production process,
d. the optical brightening of papers in the stock, or surface treatment of the formed papers,
b. being the particularly preferred application.

The optical brightening is effected in accordance with methods known per se, the application conditions being dependent on the substrate and the method of application.

When using the compounds from a long bath, to brighten, e.g., cotton, 0.05 to 0.8% of the optical brightener, in relation to the substrate, are preferably used. The bath length is preferably in a ratio of 1:10 to 1:50 and the treatment temperature preferably in the range of 30° to 60°C. The bath may contain other conventional additives.

For the brightening of paper in the stock, the compounds of formula I are preferably used in the range of 0.01 and 0.5%, based on air-dried cellulose, and may be applied in the presence of fillers, pigments or sizing agents. A particular advantage of the compounds of formula I when used to brighten paper in the stock is their notable substantivity towards cellulose fibres and the resulting notable effectiveness as well as notable stability towards acids and multi-valent cations, such as aluminium cations.

Further, the compounds of formula I are particularly suitable for incorporating in washing powders. Suitable washing powders comprise non-ionic, surface-active compounds or mixtures thereof. Besides the detergent raw materials, the washing powders may contain neutral or alkaline inorganic salts such as for example sodium sulphate, sodium carbonate, potassium carbonate, sodium phosphate, sodium water glass, magnesium silicate, sodium borate, etc., or protective colloids such as sodium bipolyphosphate, carboxy methyl cellulose and/or bleaching agents such as sodium perborate.

The amount of the brightener of formula I, in relation to the washing powder composition, is preferably in the range of 0.01 to 1%, preferably of 0.02 to 0.1%.

The compounds of formula I substantially meet the following requirements of optical brighteners in modern washing powder compositions:

1. Good efficiency (i.e., high substantivity);
2. A moderate capacity of accumulation, i.e., no discoloration of white washing when used repeatedly (multi-fold wash);
3. Non-discoloration of the washing powder during storage in an humid atmosphere;
4. Good affinity in cold;

5. Good solubility.

The compounds of formula I are well soluble in water, particularly in ammonium and alkali metal salt form, show a notable capacity of cold retention and do not develop a yellow tint on the washing powder compositions during storage in an humid atmosphere. The compounds of formula I do not require an additional process for the conversion into a crystalline form which is fast to light.

The invention is illustrated by the following Examples, in which all parts and percentages are by weight and the temperatures in degrees centigrade.

EXAMPLE 1

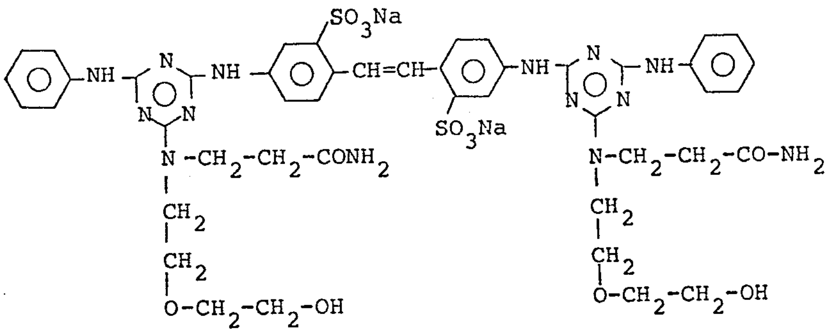

A solution of 100 parts of cyanuro chloride in 400 parts of acetone is run with stirring, over the course of 10 minutes, into 1200 parts of ice water. A solution of 96 parts of 4,4′-diaminostilbene-2,2′-disulphonic acid and 56 parts of calcined soda in 800 parts of water is added dropwise at 0° to 5° with stirring, over the course of 1 hour to the resulting suspension. The mixture is then stirred for 1 hour, i.e., until the amine is virtually fully reacted. 50 Parts of aniline are then added to the dispersion of the resulting di-Na-salt of the 4,4′-bis-[2″,4″-dichloro-s-triazinyl-(6″)-amino]-stilbene-2,2′-di-sulphonic acid and the mixture is allowed to warm to 40° over 1 hour, during addition of 210 parts of 10% sodium hydroxide solution. A solution of 98 parts of 3-[2′-(2″-hydroxy-ethoxy-amino]-propionic acid amide in 50 parts of water is then added. After distillation of the acetone, the mixture is heated to 95°–100° over the course of 3 hours by gradually adding 210 parts of 10% sodium hydroxide solution. The pH is in the range of 7.5 to 8.5. The product is dissolved by diluting it with 15,000 parts of hot water. It is subsequently filtered and precipitated after the addition of 500 parts of sodium chloride and 80 parts of 50% sulphuric acid. The product is then filtered by suction in the cold, the residue mixed with 800 parts of water and stirred. The pH is neutralized to 9 by the addition of approximately 70 parts of 30 % sodium hydroxide solution and the resulting solution of the brightener of the above formula is evaporated to dryness under vacuum. A light yellow powder which may readily be dissolved in water is obtained.

EXAMPLE 1*a*

The compound produced in Example 1, above, may also be produced as follows:

100 Parts of finely powdered cyanuro chloride are added with stirring to a mixture of 144 parts of ice-cold water, 72 parts of ice and 0.2 parts of a 30% aqueous solution of lauryl dimethylamine oxide and the mixture is stirred for 3 minutes. A solution of 52 parts of 97% aminobenzene and 66.3 parts of 30% hydrochloric acid in 144 parts of ice-cold water is added dropwise to the resulting suspension at 0° over the course of 45 minutes. The pH of the suspension is subsequently adjusted to 2 by the dropwise addition of approximately 400 parts of sodium hydroxide solution. The mixture is then stirred for 2 hours, the internal temperature is then allowed to rise to 20° and the pH is simultaneously kept constant at 2. The test for diazotizable amine should be negative or, at the most, weakly positive. The pH of the suspension is adjusted to 6 by the addition of 10% sodium hydroxide solution. A solution of 96 parts of 4,4′-diaminostilbene-2,2′-disulphonic acid and 56 parts of calcinated soda in 800 parts of water is run into the suspension over the course of 10 to 20 minutes. The pH of the mixture is in the range of 6 to 7. The temperature is then raised to 65° over the course of 1 hour. The mixture is stirred at this temperature for approximately one further hour, i.e., until the diazo test for free amine is negative. A solution of 98 parts of 3-[2′-(2″-hydroxyethoxy)-ethyl-amino]-propionic acid amide in 50 parts of water is subsequently added and the mixture is heated to 95°–100° over the course of 3 hours by gradually adding 210 parts of 10% sodium hydroxide solution.

Purification and isolation of the resulting product are effected in the way described in Example 1.

EXAMPLE 2

A brightener with similar properties is obtained by processing as in Example 1 or 1*a* but replacing the 98 parts of 3-[2′-(2″-hydroxyethoxy)-ethyl-amino]-propionic acid amide with 85 parts of 3-[2′-(2″-hydroxyethoxy)-ethyl-amino]-propionitrile.

The above-mentioned propionic acid amide or propionitrile is obtained by reacting 39.5 parts of acrylic amide in 58.8 parts of 2-(2′-hydroxyethoxy)-ethylamine-1 or 28.5 parts of acrylonitrile in 56.6 parts of 2-(2′-hydroxyethoxy)-ethyl-amine-1 at 40° and stirring at this temperature for 1 hour.

Similarly products of the following Table are obtained by replacing the aniline, employed in the above Examples, by the corresponding substituted anilines.

Table I

| Example | $R_1$ | $R_2$ |
|---|---|---|
| 3 | p-$CH_3$ | —CO—$NH_2$ |
| 4 | m-$CH_3$ | —CO—$NH_2$ |
| 5 | o-$CH_3$ | —CO—$NH_2$ |
| 6 | p-O—$CH_3$ | —CO—$NH_2$ |
| 7 | p-Cl | —CO—$NH_2$ |
| 8 | m-Cl | —CO—$NH_2$ |
| 9 | p-$SO_3Na$ | —CO—$NH_2$ |
| 10 | m-$SO_3Na$ | —CO—$NH_2$ |
| 11 | p-$CH_3$ | —C≡N |
| 12 | m-$CH_3$ | —C≡N |
| 13 | o-$CH_3$ | —C≡N |
| 14 | p-$OCH_3$ | —C≡N |
| 15 | p-Cl | —C≡N |

Table I-continued

| Example | $R_1$ | $R_2$ |
|---|---|---|
| 16 | m-Cl | $-C\equiv N$ |
| 17 | $p-SO_3Na$ | $-C\equiv N$ |
| 18 | $m-SO_3Na$ | $-C\equiv N$ |

All products form a light yellow powder which is readily dissolved in water.

APPLICATION EXAMPLE A 0.02% of the brightening agent of Example 1 are added in conventional manner to a washing powder which contains approximately 50% of soap and other conventional ingredients, such as complex forming phosphates, soda and alkali silicates. Textiles consisting of cotton are washed in conventional manner at temperatures in the range of 60° to 80° with the resulting washing powder. The textiles show an excellent white effect. Similar brightening effects are obtained by replacing the brightener of Example 1 by the brighteners of Examples 2 to 18.

The washing powder shows no discoloration when stored in an humid atmosphere.

APPLICATION EXAMPLE B 0.05% of the compound of Example 1 are added in conventional manner to a mild washing agent for fine garments which consists of approximately 30% of synthetic, detergent compounds, e.g., Na-dodecyl-benzene sulphonate and/or Na-lauryl sulphate, 5 to 10% of complex forming phosphates, e.g., Na-tripolyphosphate and 65 to 60% of sodium sulphate decahydrate. The washing powder shows an excellent brightening effect and no discoloration takes place when stored in an humid atmosphere. Cellulose washed at 70° with this washing powder shows a strong brightening effect.

A washing powder containing 0.01 to 0.05% of the compounds of Examples 2 to 18 shows the same properties.

APPLICATION EXAMPLE C

To a suspension of 100 parts of bleached sulphite cellulose in 4000 parts of water, ground in a hollander engine to 40°-Schopper-Riegler, is added a solution of 0.3 parts of a brightener of Example 1 in 300 parts of water. The solution is intensely mixed and treated over the course of 30 minutes while shaking it vigorously. The cellulose mass is subsequently sized in conventional manner with 2 parts of colophonium resin and 3 parts of aluminium sulphate. The mass is diluted with water to 20,000 parts and processed into paper sheets. The paper shows a strong brightening effect. The brightening agents of Examples 2 to 18 may be employed in the same manner.

APPLICATION EXAMPLE D

A sized paper of sulphite cellulose is coated with a coating paste consisting of 30 parts of kaolin
10 parts of barium sulphate
33.8 parts of water
20 parts of a 20% casein solution
1 part of a 20% ammonia solution
5 parts of a 10% polyvinyl alcohol solution
0.2 parts of a brightener obtained in accordance with Example 1.

An intensely white paper is obtained.

What is claimed is:

1. A compound of formula I,

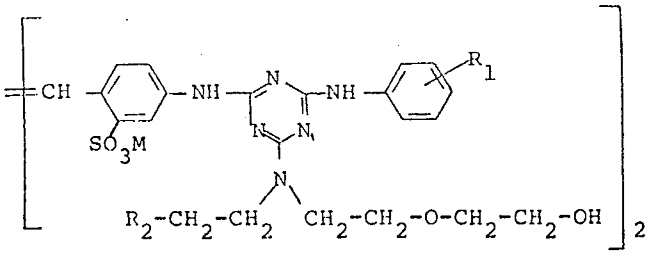

I in which $R_1$ is hydrogen, fluorine, bromine, chlorine, $C_{1-6}$alkyl, $C_{1-6}$alkoxy or $-SO_3M$,
$R_2$ is cyano or $-CONR_3R_4$,
in which either $R_3$ and $R_4$, independently, each is hydrogen, $C_{1-6}$ alkyl or $C_{2-6}$ hydroxyalkyl,
or $R_3$ and $R_4$, together with the nitrogen atom to which they are attached, form pyrrolidino, piperidino or morpholino, and
M is hydrogen or a non-chromophoric cation.

2. A compound of claim 1, wherein $R_1$ is chlorine, $C_{1-4}$alkoxy, $C_{1-4}$alkyl, hydrogen or $-SO_3M$, where M is as defined in claim 1.

3. A compound of claim 2, wherein $R_1$ is chlorine, $C_{1-4}$alkoxy, $C_{1-4}$alkyl or hydrogen.

4. A compound of claim 3, wherein $R_1$ is $C_{1-4}$alkyl or hydrogen.

5. A compound of claim 4, wherein $R_1$ is methyl or hydrogen.

6. A compound of claim 1, wherein $R_2$ is cyano or $-CONH_2$.

7. A compound of claim 2, wherein $R_2$ is cyano or $-CONH_2$.

8. A compound of claim 3, wherein $R_2$ is cyano or $-CONH_2$.

9. A compound of claim 4, wherein $R_2$ is cyano or $-CONH_2$.

10. A compound of claim 5, wherein $R_2$ is cyano or $-CONH_2$.

11. A compound of claim 6, wherein $R_2$ is cyano.

12. A compound of claim 6, wherein $R_2$ is $-CONH_2$.

13. A compound of claim 7, wherein $R_2$ is cyano.

14. A compound of claim 7, wherein $R_2$ is $-CONH_2$.

15. A compound of claim 8, wherein $R_2$ is cyano.

16. A compound of claim 8, wherein $R_2$ is $-CONH_2$.

17. A compound of claim 9, wherein $R_2$ is cyano.

18. A compound of claim 9, wherein $R_2$ is $-CONH_2$.

19. A compound of claim 10, wherein $R_2$ is cyano.

20. A compound of claim 10, wherein $R_2$ is $-CONH_2$.

21. A compound of claim 20, of formula

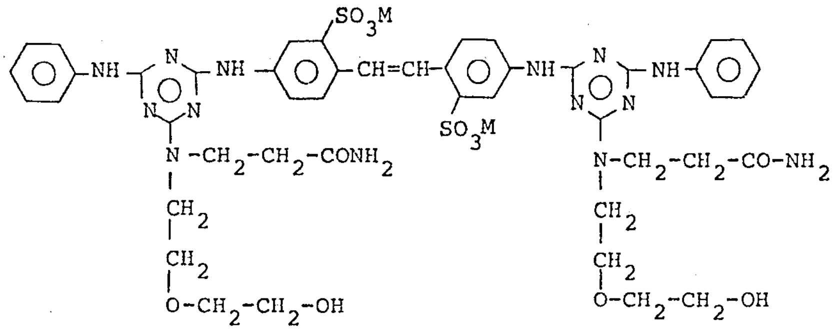

wherein M is as defined in claim 20.

22. A compound of claim 19, of formula

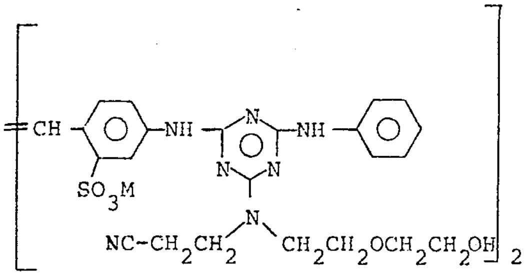

wherein M is as defined in claim 19.

23. A compound of claim 20, of formula

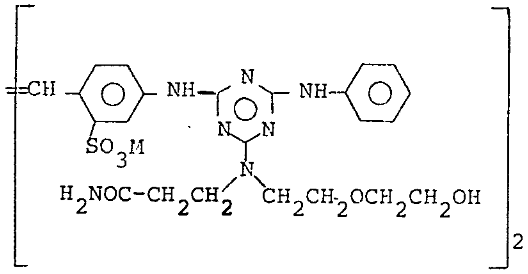

wherein M is as defined in claim 20.

24. A compound of claim 20, of formula

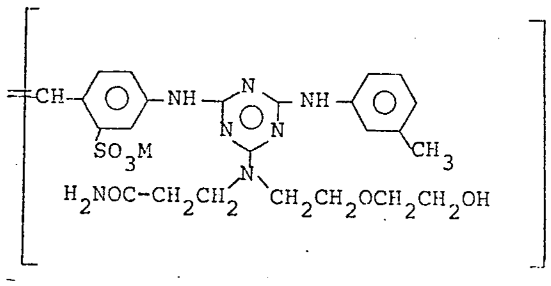

wherein M is as defined in claim 20.

25. A compound of claim 20, of formula

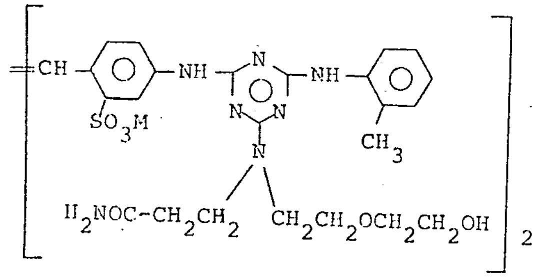

wherein M is as defined in claim 20.

26. A compound of claim 19, of formula

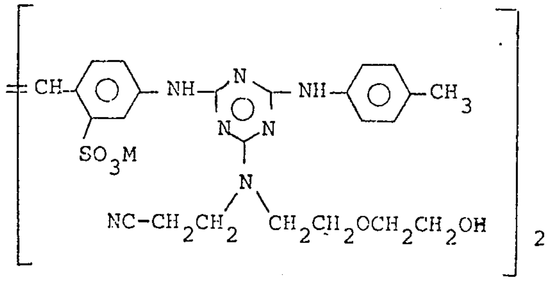

wherein M is as defined in claim 19.

27. A compound of claim 19, of formula

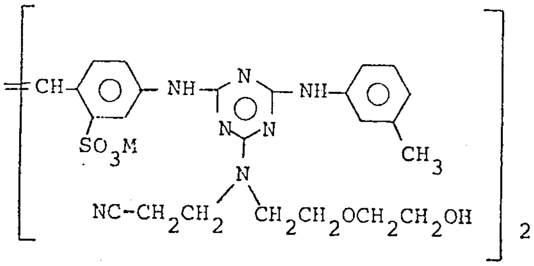

wherein M is as defined in claim 19.

28. A compound of claim 19, of formula

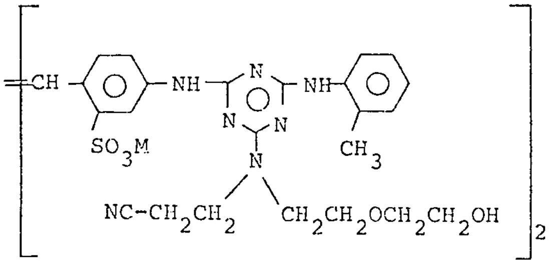

wherein M is as defined in claim 20.

29. A compound of claim 1, wherein M is a hydrogen atom, an alkali-metal cation, an alkaline earth metal cation or a cation of formula $R_5R_6R_7N^+H$, wherein $R_5$, $R_6$ and $R_7$, independently, are hydrogen or a $C_{1-4}$alkyl radical, unsubstituted or substituted by up to two hydroxy groups.

30. A compound of claim 29, wherein M is a hydrogen atom or a sodium cation.

31. A compound of claim 30, wherein M is a sodium cation.

32. A compound of claim 21, wherein M is hydrogen or a sodium cation.

33. A compound of claim 22, wherein M is hydrogen or a sodium cation.

34. A compound of claim 23, wherein M is hydrogen or a sodium cation.

35. A compound of claim 24, wherein M is hydrogen or a sodium cation.

36. A compound of claim 25, wherein M is hydrogen or a sodium cation.

37. A compound of claim 26, wherein M is hydrogen or a sodium cation.

38. A compound of claim 27, wherein M is hydrogen or a sodium cation.

39. A compound of claim 28, wherein M is hydrogen or a sodium cation.

* * * * *

UNITED STATES PATENT OFFICE

CERTIFICATE OF CORRECTION

Patent No. 3,956,283 Dated May 11, 1976

Inventor(s) Fritz Fleck

It is certified that error appears in the above-identified patent and that said Letters Patent are hereby corrected as shown below:

Title page, between items [21] and [52]

insert --[30] Foreign Application Priority Data

May 22, 1973 Switzerland 7256/73--.

Signed and Sealed this

Eighth Day of February 1977

[SEAL]

*Attest:*

RUTH C. MASON
*Attesting Officer*

C. MARSHALL DANN
*Commissioner of Patents and Trademarks*